the present invention relates to a process to prepare a compound of formula (I) wherein Y and Z can be identical or different and represent a halogene. The bis-triazole compounds of formula (I) and intermediates have antifungal activity.

United States Patent

Karimian et al.

Patent Number: 6,063,933
Date of Patent: May 16, 2000

[54] PROCESS FOR THE MANUFACTURE OF BIS-TRIAZOLE COMPOUNDS AND INTERMEDIATES USEFUL IN THE MANUFACTURE THEREOF HAVING ANTIFUNGAL ACTIVITY

[75] Inventors: Khashayar Karimian, 18 Pine Cliff Drive, Mississauga, Canada, L5N 3X1; Tim F. Tam, 155 Veneto Drive, Woodbridge, Canada, L4L 8X6; John F. Braganza, 60 Craik Rue, Chateauguay, Canada, J6J 3K6; Yuri Goldberg, 300 Antibes Drive, Apt. 1618, North York, Canada, M2R 3N8; Salvatore Zinghini, 231 Matthew Drive, Woodbridge, Canada, L4L 9B4

[73] Assignees: Khashayar Karimian; Tim F. Tam; John F. Braganza; Yuri Goldberg; Salvatore Zinghini, all of Ontario, Canada

[21] Appl. No.: 09/000,139

[22] PCT Filed: Jul. 17, 1996

[86] PCT No.: PCT/CA96/00483

§ 371 Date: Feb. 24, 1998

§ 102(e) Date: Feb. 24, 1998

[87] PCT Pub. No.: WO97/03971

PCT Pub. Date: Feb. 6, 1997

[30] Foreign Application Priority Data

Jul. 17, 1995 [NZ] New Zealand ............................ 272586

[51] Int. Cl.$^7$ .................................................. C07D 249/08
[52] U.S. Cl. ............................................................ 548/266.6
[58] Field of Search ........................................... 548/266.6

[56] References Cited

FOREIGN PATENT DOCUMENTS

| 1 182 822 | 2/1985 | Canada . |
|---|---|---|
| 1 181 076 | 1/1995 | Canada . |
| 2 106 032 | 11/1995 | Canada . |
| 0 096 569 | 12/1983 | European Pat. Off. . |
| 0 427 061 | 5/1991 | European Pat. Off. . |
| 0 618 198 | 10/1994 | European Pat. Off. . |
| 95 07895 | 3/1995 | WIPO . |
| WO 95/07895 | 3/1995 | WIPO . |

OTHER PUBLICATIONS

Murai et al, "Reduction of Epoxides", Comprehensive Organic Synthesis 8:871–893 (1991).

McKillop et al, "Sodium Perborate and Sodium Percarbonate: Cheap, Safe and Versatile Oxidising Agents for Organic Synthesis", Tetrahedron 51(22):6145–6166 (1995).

*Primary Examiner*—Patricia L. Morris
*Attorney, Agent, or Firm*—Nixon & Vanderhye P.C.

[57] ABSTRACT

The present invention relates to a process to prepare a compound of formula (I) wherein Y and Z can be identical or different and represent a halogene. The bis-triazole compounds of formula (I) and intermediates have antifungal activity.

18 Claims, No Drawings

PROCESS FOR THE MANUFACTURE OF BIS-TRIAZOLE COMPOUNDS AND INTERMEDIATES USEFUL IN THE MANUFACTURE THEREOF HAVING ANTIFUNGAL ACTIVITY

FIELD OF INVENTION

This invention relates to a novel process for the manufacture of bis-triazole derivatives and in particular for the preparation of 2-2,4fluorophenyl)-1,3-bis-(H-1,2,4-triazol-1-yl)-propan-2-ol known as fluconazole, and novel intermediates useful in the manufacture of such bis-triazole compounds, of formulae (IV) and (V):

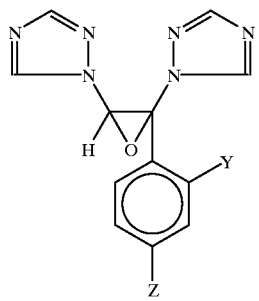

IV

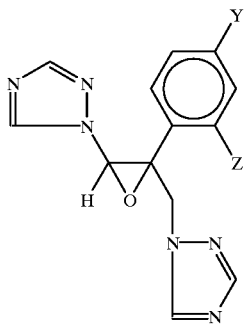

V

BACKGROUND OF INVENTION

Among the bis-triazole compounds, fluconazole, ie. 2-(2,4-difluorophenyl)-1,3-bis-(1H-1,2,4triazol-1-yl)-propan-2-ol has antifungal activity.

Fluconazole has been prepared by three methods:

In Canadian Patent 1,181,076 a Friedel-Crafts acylation of 1,3difluorobenzene with chloroacetyl chloride results in the formation of 2,4difluoro- -chloroacetophenone which is then reacted with 1,2,4-triazole to afford 2.4difluoro- -(1H-1,2,4-triazol-1-yl)acetophenone. The resulting ketone is subjected to a Corey-Chugaev reaction with trimethyl sulfoxonium iodide to form 2-(2,4difluorophenyl)-3-(1H-1,2,4-triazol-1-yl)-1,2-epoxypropane. Condensation of the resulting epoxide with 1,2,4-triazole affords fluconazole. The overall yield is between 4–8% (Scheme 1).

The preparation can be depicted in the following scheme:

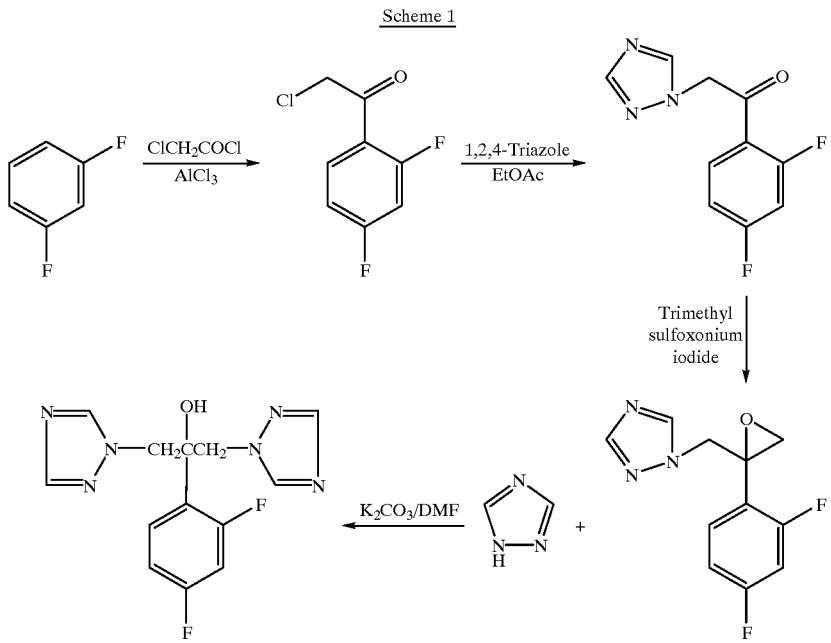

Scheme 1

In Canadian Patent 1,181,076, 1-iodo- or 1-bromo-2,4-difluorobenzene is converted to its Grignard or lithiated organometallic complex which is then reacted with 1,3-dichloroacetone to afford 1,3-dichloro-2-(2,4difluorophenyl)-2-propanol. The resulting chlorohydrine is then reacted with two moles of 1,2,4-triazole to afford fluconazole. The last transformation involves the formation of 2-2,4-difluorophenyl)-3-(1H-1,2,4triazol-1-yl)-1,2-epoxypropane as an intermediate as seen in scheme 1.

The process is illustrated in the following scheme:

In Canadian Patent 1,182,822. 1,3-dichloroacetone is reacted with two moles of 1,2,4triazole to afford 1,3di(triazolylacetone). The resulting ketone undergoes a Grignard reaction to lead to fluconazole, as depicted in the following scheme:

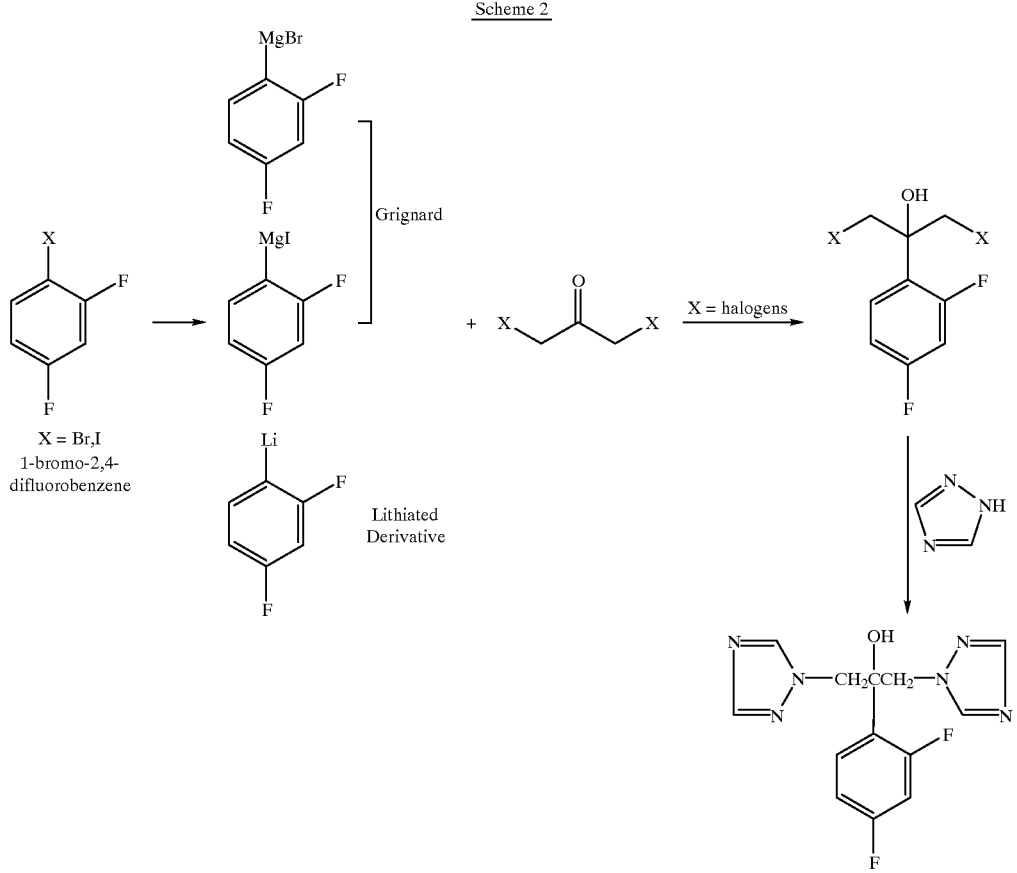

Scheme 2

Scheme 3

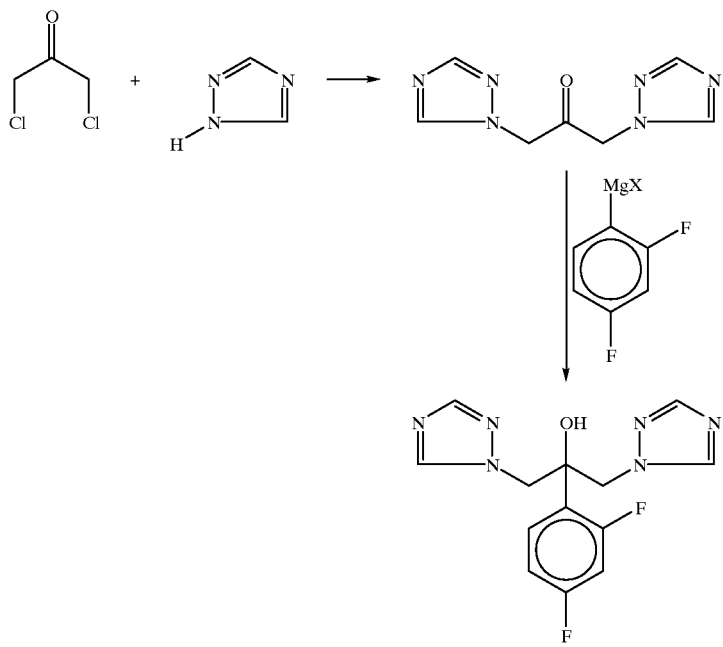

In the present application, there is disclosed a process which involves the epoxidation of triazol-containing olefins, followed by reduction of the epoxide obtained to afford fluconazole. The present process offers numerous advantages over the existing art.

First, it allows the obtention of the bis-triazole compounds and specifically fluconazole in considerably higher yields than the existing procedures.

Second, the process is easy to scale up, avoiding the use of a Grignard reaction and a Corey-Chugaev reaction which are extremely air and moisture sensitive and therefore difficult to carry out in large scale.

Third, it does not entail the use of ethers which are extreme fire hazards.

Forth, it results in avoiding the use of highly toxic and corrosive substances such as dichloroacetone and chloroacetyl chloride.

Fifth, the process allows for the formation of a series of unknown epoxide analogues of fluconazole with potential therapeutic value.

Therefore, one object of the present invention is to provide a convenient novel process for the production of bis-triazole derivatives and specifically fluconazole.

It is a further object of the invention to produce new intermediates useful in the manufacture of such bis-triazole compounds. The resulting intermediates are obtained in high yields.

SUMMARY OF THE INVENTION

According to the present invention, a process is provided for preparing bis-triazole derivatives which comprises the steps of converting the E and/or Z olefins (II) and (III) to their corresponding epoxides (IV) and (V) which are then reduced to the bis-triazole compounds of formula (I). The process is depicted as follows:

Scheme 4

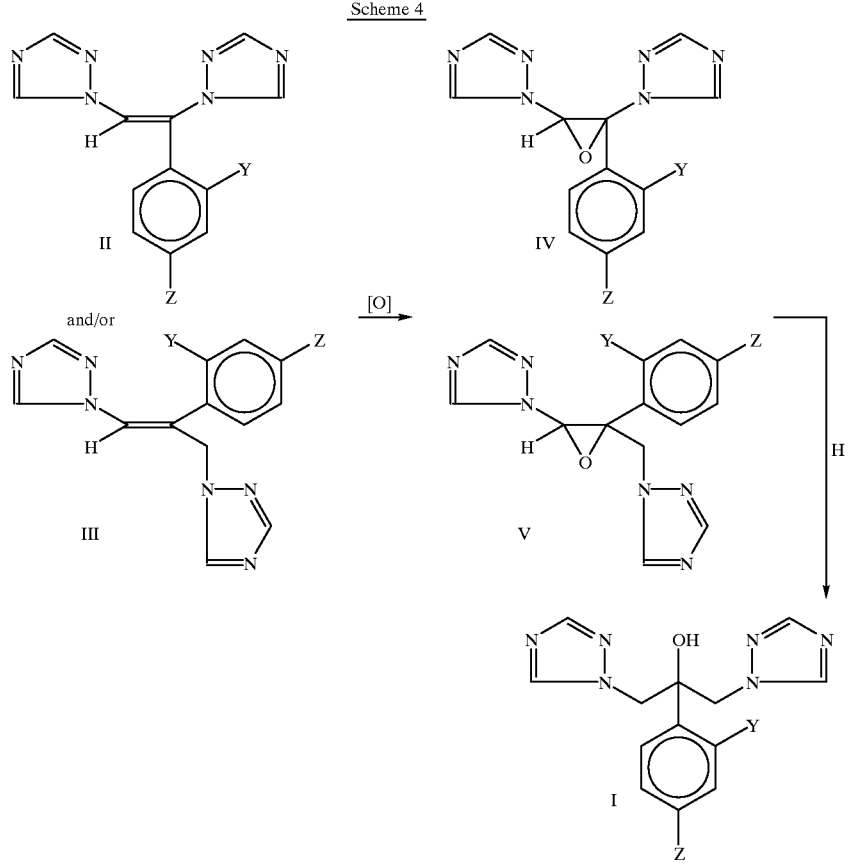

The present invention also provides for novel intermediates in the form of epoxides (IV) and (V) which may be conveniently reduced to bis-triazole compounds under the influence of a variety of reducing agents. In a preferred embodiment, the process allows for the preparation of fluconazole.

In another preferred embodiment the invention entails the epoxide intermediates.

The starting materials (II) and (III) for the process to manufacture the bis-triazole compounds (I), (IV) and (V) have been prepared according to the method described in Canadian Patent Application 2,106,032. Canadian Patent Application 2,106,032 specifically describes the synthesis of (EZ)-1,3-bis-(1H-1,2,4-triazol-1-yl)-2-(2,4difluorophenyl)-1-propene. (II) and (III). A similar method was followed to prepare the (EZ)-1,3-bis-(1H-1,2,4-triazole-1-yl)-2-(2,4-dihalophenyl)-1-propene compounds. The olefins may be formed in different ratios depending on the solvent used. The E and Z-olefins (II) and (III) may be interconverted by isomerization under various conditions. For example, treatment of a mixture of isomers with a base or UV irradiation gives rise to a mixture containing a higher ratio of Z to E isomer. On the other hand, treatment of the mixture with sodium hydroxide and hydrogen peroxide in methanol increases the amount of the E isomer. The E and the Z isomer of the olefins (II) and (III) may be separated by conventional chromatographic methods or by crystallization eg. methylisobutylketone (MIK) or a mixture thereof.

It has been observed that both olefins are extremely resistant to a variety of known chemical transformations that are commonly used for double bond manipulations. For example, treatment of the E olefin (II) with meta-chloroperoxybenzoic acid (m-CPBA) in dichloromethane results in 10–15% of the epoxide (IV). The use of higher boiling solvents such as dichloroethane, tetrachloroethane, chlorobenzene, and glacial acetic acid does not affect the yield rather it results in the conversion of the olefins to other by-products.

In the present invention, the epoxidation reaction of the E and/or Z olefins (II), (III) is carried out under aqueous conditions in the presence of a peracid or a peroxide and a base. Suitable peracids are peracetic acid, perbenzoic acid, m-CPBA. Examples of peroxides are hydrogen peroxide, sodium percarbonate and the like as described in McKillop, Tetrahedron, 51, p. 6145, 1995. Any base capable of salt formation with the acid generated from the reduction of the peracid by the olefin may be used. The E-isomer (II) is considerably more reactive than the Z-isomer (III) during the epoxidation reaction with peracids. Most preferably the peracid is m-CPBA and the salt forming base is potassium bicarbonate. In the preferred reaction the pH of the reaction medium is controlled so as to be below the pKa of the acid generated from the reduction of the corresponding peracid eg. m-CPBA, $pk_a$=10. The transformation is essentially complete in the case of the E-isomer (II) in 100% yield within a few hours, while huge excess of m-CPBA is required in order to obtain 60–80% yield for epoxidation of the Z-olefin (III).

The Z-isomer (III) is considerably more reactive than the E-isomer (II) during the epoxidation reaction with peroxide. The epoxidation of the Z-olefin (III) can be affected with peroxide, aryl nitrile or alkyl nitrile in the presence of a base in a protic solvent. The most preferred condition for this transformation involves the use of $H_2O_2$, benzonitrile and $KHCO_3$ in methanol at room temperature for a period of 72–96 hours with pH of the reaction being maintained between 8–12 and preferably between 8.5–9.5.

The addition of oxygen to the double bond of the E and/or the Z-isomer may occur from the re or the si face of the olefins. However, the resulting epoxides in each case, while diastereomers, are enantiomers of each other and therefore magnetically equivalent in NMR spectroscopy. Therefore, in our invention, epoxide (IV) covers both enantiomers derived from the E olefin and epoxide (V) covers both enantiomers derived from the Z olefin (III).

The epoxidation of a mixture of the E olefin (II) and the Z olefin (III) proceeds at different rates with respect to each olefin depending on the epoxidation conditions such as solvent, epoxidizing agent

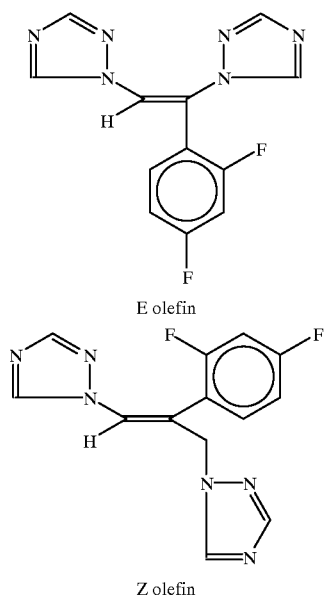

E olefin

Z olefin

The epoxides (IV) and (V) are then subjected to a variety of reduction reactions such as lithium aluminum hydride (LAH), diisobutyl aluminium hydride (DIBAL), lithium borohydride, hydrogen and Raney nickel, palladium/barium sulfate with cyclohexene, sodium cyanoborohydride/ borontrifluoride etherate, zinc/glacial acetic acid and the like as illustrated in Murai "Comprehensive Organic Synthesis", Vol 8, p. 871, 1991). Most preferably diisobutyl aluminum hydride is used.

The present invention will be more fully understood by the following examples which illustrate the invention, but are not to be considered limiting to the scope of the invention.

EXAMPLE 1

Separation of (E-) and (Z-) 1,3-Bis(1H-1,2,4-triazol-1-yl)-2-(2,4-difluorophenyl)-1-propene (II and III, respectively) by Fractional Crystallization.

250 g of a 60:40 Z/E mixture of isomers was dissolved in 375 ml MIK and heated to about 90° C. The resulting solution was cooled to room temperature and 375 ml of hexane was added with good agitation. An additional 150 ml of MIK was added and the resulting solution was seeded with pure Z isomer (III) and stirred at room temperature for 5 hrs. The resulting crystalline mass was filtered and washed with 3×30 ml of a 60:40 mixture of MIK/hexane and dried under vacuum to a constant weight to afford 120 g of virtually pure Z isomer (III). The mother liquor was concentrated to an oil, 18 g of which was injected on a Waters Prep 500 Silica Gel column and eluted with 99:1 mixture of ethyl acetate-methanol. The pure fractions were pooled and evaporated to afford 10 g of pure E (II) and 5 g of pure Z isomer (III).

E isomer (II):

mp 83.8–85.2° C.

$^1$H-NMR (CDCl$_3$) δ (ppm): 5.74 (s, 2H), 6.80 (m, 2H), 7.09 (s, 1H), 7.15 (m,1H), 7.76 (s, 1H), 8.08 (s, 1H), 8.09 (s, 1H), 7.18 (s, 1H).

IR(KBr,cm$^{-1}$): 1137, 1590, 1667, 3039, 3069, 3103, 3123

Elemental Analysis, Calculated: C 54.17; H 3.50; N 29.15, Found. C 53.51; H 3.37; N 29.29

Z isomer (III):

mp 98–100° C., $^1$H-NMR (CDCl$_3$) δ (ppm): 5.08 (s, 2H), 6.78 (m, 3H), 7.26 (s, 1H), 7.67 (s, 1H), 7.79 (s, 1H), 7.85 (s, 1H), 7.92 (s, 1H).

IR (KBr.cm$^{-1}$): 1138, 1507, 1593, 1617, 1692, 3086, 3131

Elemental Analysis, Calculated: C 54.17; H 3.50; N 29.15. Found: C 53.78; H 3.35; N 29.34

EXAMPLE 2

Conversion of the E-Isomer (II) to the Z-Isomer (III).

A. Conversion of E to Z isomer with strong base.

The E isomer (100 mg) was suspended in 5 ml of a 10% solution of sodium hydroxide. The mixture was refluxed for 5 hours at which time the conversion was 75% complete.

B. Conversion of E to Z isomer with weak base.

A mixture of E and Z-olefins (II:III=3:1) (288 mg, 1 mmol) was suspended in a solution of KHCO$_3$ (10 mg, 0.1 mmol) in water (5 ml). The mixture was heated to reflux for 14 hrs. NMR analysis showed that the II:III ratio changed from 3:1 to 1:3.

C. Conversion of E to Z isomer with UV irradiation.

The E isomer (200 mg ) was dissolved in 150 ml of 1,2-dichloroethane and irradiated with a Canrad-Hanovia 7825 mercury-vapour UV immersion lamp. The conversion was 35% complete in 0.5 hr as assayed by TLC and HPLC analyses.

D. Conversion of Z to E isomer with strong base.

A 13:1 mixture of Z:E olefins (500 mg, 1.74 mmol) was dissolved in 5 ml of methanol. To the resulting solution was added 0.8 ml of 10% sodium hydroxide followed by the addition of 0.3 ml of 30% hydrogen peroxide. Reaction was stirred for 48 hrs at room temperature. NMR analysis showed that the II:III ratio changed from 1:13 to 1:1.

TLC 80% EtOAc: 10% MeOH: 10% NH$_4$OH; E-isomer, R$_f$=0.27, Z-isomer, R$_f$=0.44.

HPLC 80% CH$_3$CN :20% 8.6 mM NH$_4$H$_2$PO$_4$, flow rate=1.5 ml/min, Zorbax RX C18, 15 cm×4.6 =m; E-isomer, R$_τ$=9.9 min, Z-isomer R$_{96}$=4.8 min.

EXAMPLE 3

A. Preparation of (R,S),(S,R)-2-2,4-Difluorophenyl)-1,3-bis-(1H-1,2,4-triazol-1-yl)-2,3-epoxypropane (IV).

The E-isomer (II) (5 g, 17.4 mmol) was dissolved in methylene chloride (50.5 ml). Water (50 ml) was added, followed by the addition of potassium bicarbonate (5.6 g, 55.6 mmol) and mCPBA (Aldrich) (9.6 g, 55.6 mmol). The mixture was stirred at room temperature for 4 hours by which time the conversion was 77% complete. More potassium bicarbonate (2.8 g, 27.8 mmol) was added, followed by the addition of m-CPBA (4.8 g, 27.8 mmol). The mixture was stirred at room temperature for 14 hours by which time the conversion was 100% complete. The organic sovent was removed under reduced pressure and the resulting oil was dissolved in ethyl acetate (50 ml). The organic layer was separated and the aqueous layer was washed with 4×100 ml portions of ethyl acetate. The combined organic layer was washed with 2×20 ml of a 10% solution of sodium hydrogen sulfite and then with 5×30 ml portions of a 10% solution of sodium hydroxide. The organic layer was dried over sodium sulfate, filtered and evaporated to an oil under reduced pressure. The crude epoxide (4.1 g) was injected to a Waters Prep 500 Silica Gel Column and eluted with a 99:1 mixture of ethyl acetate-methanol. The pure fractions were pooled and evaporated to afford 2 g of pure titled compound (IV).

Epoxide (IV):

mp 121–123° C., $^1$H-NMR (CDCl$_3$) 6 (ppm): 4.79 (ABe 2H, JAB=15.1Hz), 5.36 (s, 1H), 7.12 (m, 2H), 7.27 (m, 1H), 7.82 (s, 1H), 7.99 (s, 1H), 8.15 (s, 1H), 8.54 (s, 1IE);

IR (KBr. cm$^{-1}$): 1036, 1145, 1600, 1622, 3121

Elemental Analysis. Calculated: C 51.30; H 3.31; N 27.63 Found: C 50.98, H 3.34, N 27.52.

B. Preparation of (R,S),(S,R) -2-(2,4-Difluorophenyl)-1, 3-bis-(1H-1,2,4-triazol-1-yl)-2,3-epoxypropane (IV) and (R,R),(S,S)-2-(2,4-Difluorophenyl)-1,3-bis-(1H-1,2,4-triazol-1-yl)-2,3-epoxypropane (V)

In a similar manner the Z olefin (III) was converted to a mixture of the title compounds (IV) and (V). The small quantity of the Z epoxide (V) was also formed which was separated using the chromatographic procedure described above.

Epoxide (V):

mp 79–81° C., $^1$H-NMR (CDCl$_3$) δ (ppm): 4.78 (AB$_q$, 2H, J$_{AB}$=15.1 Hz), 5.50 (s, 1H), 6.7–6.9 (m, 2H), 7.05–7.2 (m, 1H), 7.55 (s, 1H), 7.86 (s, 1H), 7.94 (s, 1H), 8.07 (s, 1H);

IR (KBr. cm$^{-1}$): 3440, 3121, 1621, 1507, 1422, 1275, 1205, 1140, 1106, 1021 cm$^{-1}$;

Elemental Analysis, Calculated: C 51.30; H 3.31; N 27.63 Found: C 51.21 , H 3.13, N 27.73.

C. Preparation of (R,S),(S,R)-2-(2,4-Difluorophenyl)-1,3-bis-(1H-1,2,4-triazol-1-yl)-2,3epoxypropane (IV) and (R,R),(S,S)-2-(2,4Difluorophenyl)-2,3-bis-(1H-1,2,4-triazol-1-yl)-2,3-epoxypropane (V).

In a similar manner a 1:1 mixture of E and Z olefins (II) and (III) were converted to epoxides (IV) and (V).

EXAMPLE 4

A. Preparation of R,R),(S,S)-2-(2,4-Difluorophenyl)-1,3-bis-(1H-1,2,4-triazol-1yl)-2,3-epoxypropane (V).

The Z-olefin (III) (5 g, 17.4 mmol) was dissolved in methanol (15 ml). Potassium bicarbonate (0.35 g, 3.48 mmol) was added followed by benzonitrile (7 ml. 70 mmol). Thirty percent hydrogen peroxide (4 ml, 34.8 mmol) was added dropwise and the mixture was stirred at room temperature for 3 hrs. More potassium bicarbonate (0.35 g) was added and stirring was continued for 40 hours. More hydrogen peroxide (4 ml, 34.8 mmol) was added and stirring was continuted for another 36 hours by which time the reaction was shown to be complete by HPLC. The reaction was quenched with 100 ml of 5% aqueous sodium hydrogen sulfite. Residual methanol was removed under reduced pressure and the aqueous mixture was acidified with 50 ml of a 5% solution of sulfuric acid. The resulting mixture was cooled to 2° C. and stirred for 24 hours. The precipitated benzamide was filtered and the filtrate was basified with sodium carbonate to pH 9–10 and extracted twice with four 50 ml portions of MIK. The organic solvent was removed under reduced pressure to obtain a light yellow oil which was crystallized from MIK/hexane to afford 4.5 g (85%) of pure Z epoxide.

EXAMPLE 5

Preparation of 2-(2,4-difluorophenyl)-1,3-bis-(1H-1,2,4-triazol-1-yl)-propan-2-ol (I)

The E epoxide (IV) (50 mg. 0.16 mmol) was dissolved in THF (1 ml) under a nitrogen atmosphere and the solution was cooled to 0° C. A 1 M solution of lithium aluminum hydride in THF (0.16 ml 0.16 mmol) was added dropwise and the mixture was stirred at room temperature for 2 hours. The mixture was quenched with 10% aqueous sodium hydroxide and worked up in the usual manner. The resulting oil was injected on a Waters Prep 500 Silica Gel column and eluted with 80:20 mixture of ethyl acetate-methanol. The pure fractions were pooled and evaporated to afford 30 mg of the titled compound (I). The identity of the product was confirmed by comparing its IR, $^{13}$C and $^1$H NMR, UV spectra as well as TLC and HPLC chromatograms with those of the authentic material.

Fluconazole (I):

mp 138–140° C.

$^1$H-NMR (CDCl$_3$) δ (ppm): 4.60 (AB$_q$, 4H, J$_{AB}$=14.3 Hz), 5.49 (s, 1H, OH), 6.76–6.82 (m, 2H), 7.41–7.45 (m, 1H), 7.86 (s, 2H), 8.06 (s, 2H);

EXAMPLE 6

Preparation of 2-(2,4-difluorophenyl)-1,3-bis-(1H-1,2,4-triazol-1-yl)-propan-2-ol (I)

A. From E epoxide (IV):

The E epoxide (IV) (1.3 g, 4.28 mmol) was dissolved in dichloromethane (30 ml) under a nitrogen atmosphere and the solution was cooled to 0° C. Diisobutylaluminium hydride (DIBAL) (1M in CH$_2$Cl$_2$, 4.7 ml, 4.7 mmol) was added via a syringe and the reaction was stirred at room temperature for 3 hours while adding 235 mL of the DIBAL solution twice after 1 and 2 hours. The reaction was quenched with 10% aqueous NaOH. The mixture was filtered to give a biphasic filtrate. The organic layer was separated, dried (MgSO$_4$) and evaporated. The oil obtained was triturated with hexane/dichloromethane to give 0.98 g of fluconazole (I) as a yellowish solid which was recrystallyzed from isopropanol. The identity of the product was confirmed by comparing its IR, $^{13}$C and $^1$H NMR, UV spectra as well as TLC and HPLC chromatograms with those of the authentic material.

B. From Z-epoxide (V):

In a similar manner as shown in example 6A, the Z epoxide (V) was reduced to fluconazole (I).

C. From a mixture of epoxides (IV) and (V):

Proceeding in the same manner as shown in example 6A, a mixture of epoxides (IV) and (V) was reduced to fluconazole (1).

What is claimed:
1. A process to prepare a compound of formula (I)

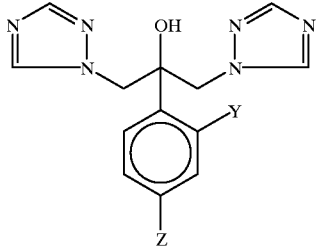

in which Y and Z can be identical or different and represent a halogen, which comprises:

(1) epoxidizing an olefin in the E configuration of formula (II):

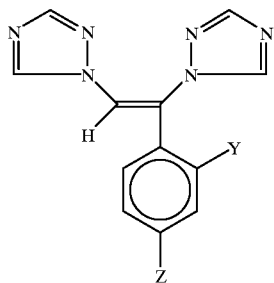

into the corresponding epoxide of formula (IV)

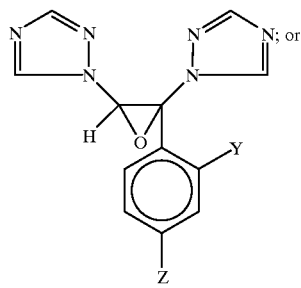

(2) epoxidizing an olefin in the Z configuration of formula (III):

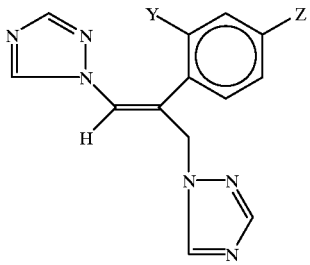

into the corresponding epoxide of formula (V)

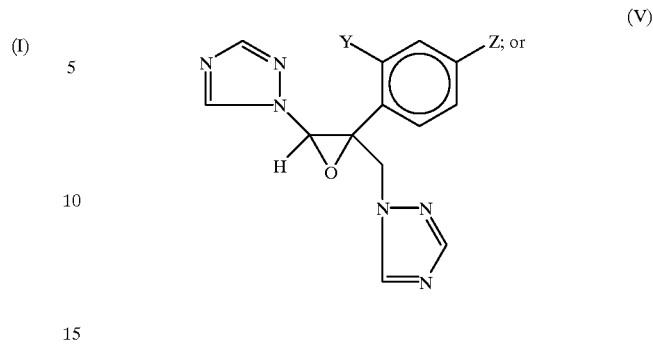

(3) epoxidizing a mixture of olefins of formula (II) and (III) into the corresponding epoxides (IV) and (V), respectively;

wherein the epoxidation is carried out in the presence of a peracid or a peroxide and a base in a protic solvent; and (4) transforming the epoxide or epoxides into the compound of formula (I) using a reducing agent.

2. The process according to claim 1, wherein the peracid is metachloroperoxybenzoic acid, perbenzoic acid or peracetic acid.

3. The process according to claim 1, wherein the base is potassium bicarbonate.

4. The process according to claim 2, wherein the pH is maintained below the pKa of the acid generated from the reduction of the corresponding peracid.

5. The process according to claim 1, wherein the peroxide is hydrogen peroxide or sodium percarbonate.

6. The process according to claim 5, wherein the pH of the reaction is between 8 to 12.

7. The process according to claim 6, wherein the pH is between 8.5 to 9.5.

8. The process according to claim 1, wherein the protic solvent is water or methanol.

9. The process according to claim 1, wherein the reducing agent is diisobutyl aluminium hydride or lithium aluminium hydride or lithium borohydride.

10. A process to prepare 2-(2,4-difluorophenyl)-1,3 bis-(1H-1,2,4-triazol-1-yl)-propan-2-ol of formula (I):

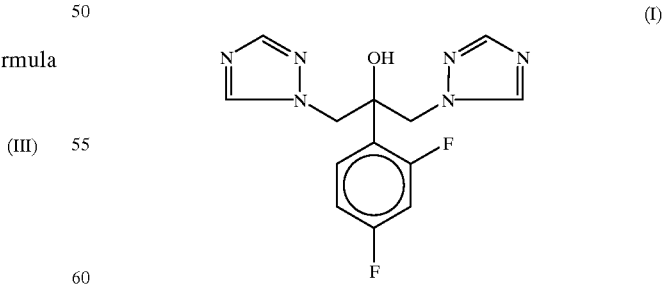

in which Y and Z are fluoro which comprises;

(1) epoxidizing (E) 1,3-bis-(1H-1,2,4-triazol-1-yl)-2-(2,4-difluorophenyl)-1-propene of formula (II):

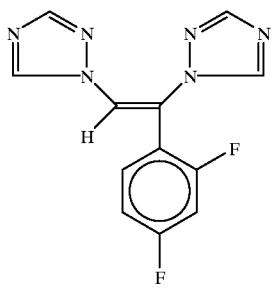

into the corresponding epoxide of formula (IV):

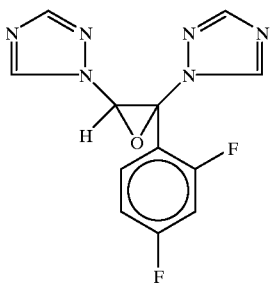

(2) epoxidizing (Z) 1,3-bis-(1H-1,2,4-triazol-1-yl)-2-(2,4-difluorophenyl)-1-propene of formula (III):

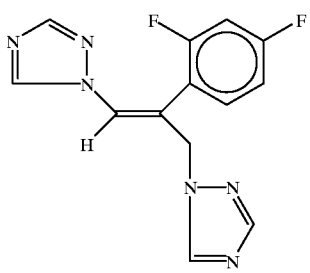

into the corresponding epoxide of formula (V):

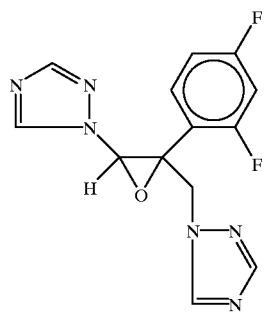

(3) epoxidizing a mixture of (E,Z) 1,3-bis-(1H-1,2,4-triazol-1-yl)-2(2,4-difluoropheayl)-1-propene into the corresponding epoxides;

wherein the epoxidation is carried out in the presence of a peracid or a peroxide and a base in a protic solvent; and (4) transforming the epoxide or epoxides into the compound of formula (I) using a reducing agent.

11. The process according to claim 10, wherein the peracid is metachloroperoxybenzoic acid, perbenzoic acid or peracetic acid.

12. The process according to claim 10, wherein the base is potassium bicarbonate.

13. The process according to claim 11, wherein the pH is maintained below the pKa of the acid generated from the reduction of the corresponding peracid.

14. The process according to claim 10, wherein the peroxide is hydrogen peroxide or sodium percarbonate.

15. The process according to claim 10, wherein the protic solvent is water or methanol.

16. The process according to claim 14, wherein the pH of the reaction is between 8 to 12.

17. The process according to claim 16, wherein the pH is between 8.5 to 9.5.

18. The process according to claim 16, wherein the reducing agent is diisobutyl aluminium hydride or lithium aluminium hydride or lithium borohydride.

* * * * *